US006740765B1

(12) United States Patent
Diederich et al.

(10) Patent No.: US 6,740,765 B1
(45) Date of Patent: May 25, 2004

(54) METHOD FOR PREPARING CYCLOHEXANE CARBOXYLIC ACIDS

(75) Inventors: Ann M. Diederich, Thorndale, PA (US); Ann Marie Eldridge, Norristown, PA (US); Robert J. Mills, Collegeville, PA (US); Vance J. Novack, Devon, PA (US)

(73) Assignee: SmithKline Beecham Corporation, Philadelphia, PA (US)

( * ) Notice: Subject to any disclaimer, the term of this patent is extended or adjusted under 35 U.S.C. 154(b) by 72 days.

(21) Appl. No.: 10/030,718

(22) PCT Filed: Aug. 4, 2000

(86) PCT No.: PCT/US00/21434

§ 371 (c)(1), (2), (4) Date: Apr. 2, 2002

(87) PCT Pub. No.: WO01/10817

PCT Pub. Date: Feb. 15, 2001

Related U.S. Application Data

(60) Provisional application No. 60/147,578, filed on Aug. 6, 1999.

(51) Int. Cl.[7] .................................................. C07F 7/08

(52) U.S. Cl. ........................ 556/406; 514/362; 558/381; 558/127

(58) Field of Search ................................. 558/406, 426, 558/127, 381; 514/362, 520, 521

(56) References Cited

U.S. PATENT DOCUMENTS

| 5,552,438 | A | * | 9/1996 | Christensen, IV | .......... 514/520 |
| 5,602,157 | A | * | 2/1997 | Christensen, IV | .......... 514/362 |
| 5,614,540 | A | * | 3/1997 | Christensen, IV | .......... 514/362 |
| 5,643,946 | A | * | 7/1997 | Christensen, IV | .......... 514/512 |

OTHER PUBLICATIONS

Dei et al, J. med. Chem., 1991, vol. 34 pp. 2219–2225.*

* cited by examiner

*Primary Examiner*—Paul J. Killos
*Assistant Examiner*—Hector M. Reyes
(74) *Attorney, Agent, or Firm*—James M. Kanagy; Stephen Venetianer; Charles M. Kinzig

(57) ABSTRACT

This invention relates to a method for preparing 4-substituted-4-cyanocyclohexane carboxylates by forming the cyclohexane ring by treating a α,α-bis(2-haloethyl)-4-benzeneacetonitrile with a dialkyl malonate and decarboxylating the resulting diester.

13 Claims, No Drawings

METHOD FOR PREPARING CYCLOHEXANE CARBOXYLIC ACIDS

This application claims the benefit of Provisional Application Ser. No. 60/147,578 filed Aug. 6, 1999.

AREA OF THE INVENTION

This invention relates to a method for preparing 4-substituted-4-cyanocyclohexancarboxylic acids. Exemplary compounds are useful as PDE 4 inhibitors.

BACKGROUND OF THE INVENTION

The process of this invention relates to making compounds which are useful in treating diseases modulated by the isoforms of the phosphodiesterase 4 enzyme. The novel intermediates and processes of this invention are useful in making acids which are known PDE 4 inhibitors. They are useful for, among other things, treating pulmonary diseases such as chronic obstructive pulmonary disease (COPD) and asthma. The compounds which are prepared by the methods of this invention are described in, for example U.S. Pat. No. 5,554,238 issued 03 Sep., 1996. That patent is incorporated here by reference in full. Those compounds, particularly the 4-cyanocyclohexanoic acids, have marked effects on neutrophil activity, inhibiting neutrophil chemotaxis and degranulation in vitro. In animal models, those compounds reduce neutrophil extravasation from the circulation, pulmonary sequestration and the edematous responses to a number inflammatory insults in vivo. They have been found to be useful in treating COPD in humans, and possibly in other mammalian species which suffer from COPD.

SUMMARY OF THE INVENTION

In a first aspect, this invention relates to a process for preparing a compound of formula (I)

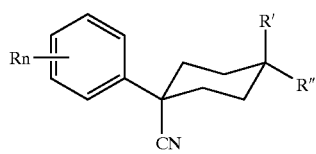

where

R is halo, $C_{1-6}$alkyl, $C_{1-6}$alkyl substituted with 1 to 4 halogens, $C_{1-6}$alkoxy, $C_{1-6}$alkenyl, —O—$(CH_2)_m$cycloalkyl of 3–6 carbons;

n is 1–5;

m is 0–6; and

R' and R" are independently hydrogen or CO(O)X where X is hydrogen or $C_{1-6}$alkyl;

which process comprises decarboxylating the diester or diacid of Formula (A)

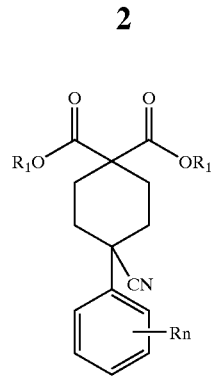

where $R_1$ is hydrogen or a $C_{1-6}$alkyl-ester forming group and R and n are the same as for Formula (I).

In a further aspect this invention relates to a compound of formula (A) per se.

In a third aspect this invention relates to preparing certain other intermediates that are useful in preparing the diester or di-acid of Formula (A), and the intermediates themselves, i.e:

a compound of Formula (B)

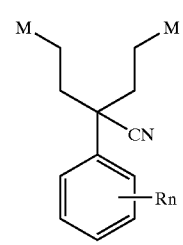

wherein R and n are the same as in Formula (I) and M is OH, an activated hydroxyl group, or halo; and a compound of Formula (C)

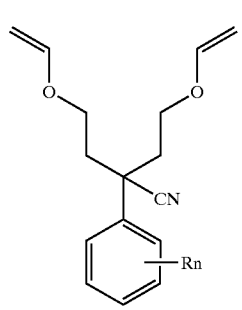

wherein R and n are the same as in Formula (I).

In yet another aspect, the invention provides a method for making a compound of Formula (C) by treating the nitrile of formula (D)

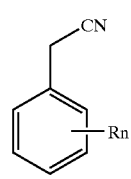

where R and n are the same as defined above, with 2-chloroethyl vinyl ether and a strong base.

This invention also provides a method for preparing a compound of Formula (I) which comprises a. converting the vinylethyl ether of Formula (C)

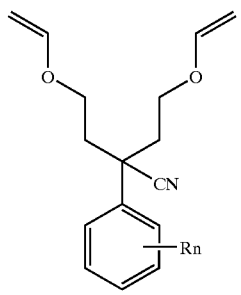

(C)

wherein R and n are halo, $C_{1-6}$alkyl, $C_{1-6}$alkyl substituted with 1 to 4 halogens, $C_{1-6}$alkoxy, $C_{1-6}$alkenyl, —O—$(CH_2)_m$cycloalkyl of 3–6 carbons;

n is 1–5;

m is 0–6;

to a compound of Formula (B)

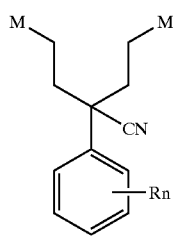

(B)

where M is OH, b. converting the hydroxyl group of Formula (B) to a compound of Formula (B) where M is a tosylate, mesylate or a triflate, c. converting the tosylate, mesylate or triflate in Formula (B) to a compound of Formula (B) where M is halo, d. treating the di-halo compound with dialkyl malonate to obtain a compound of Formula (A)

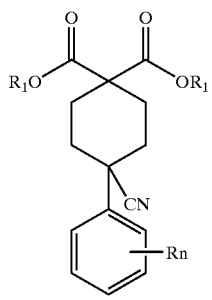

(A)

where $R_1$ is lower alkyl, e. optionally saponfying the diester of Formula (A) to obtain a compound of Formula (A) where $R_1$ is hydrogen; and f. decarboxylating a compound of Formula (A) where $R_1$ is hydrogen or $C_{1-6}$alkyl to obtain a compound for Formula (I) where one of R' is hydrogen and the other is CO(O)X where X is $C_{1-6}$alkyl or hydrogen.

SPECIFIC EMBODIMENTS OF THE INVENTION

This invention provides a method for preparing cyclohexanoic acids. In particular it provides an alternative means for preparing the cyclohexanoic acids disclosed in U.S. Pat. No. 5,554,238 where the 4-position on the cyclohexane ring has a CN group.

"Halo" as used herein includes fluoro, chloro, bromo, and iodo. "Halide" includes fluoride, chloride, bromide and iodide.

For all of the compounds disclosed herein, a preferred embodiment is one where there are two R groups, i.e. n is 2. Most preferred are those compounds where one R group is at the 3 position and the second R group is on the 4 position of the benzene ring. More particularly it is preferred that each R group be independently $C_{4-6}$cycloalkyloxy or $C_{1-2}$alkoxy unsubstituted or substituted by 1 or more halogens. More preferred are methoxy, $C_{1-2}$alkoxy substituted by up to 3 fluoro atoms, cyclopropylmethoxy or cyclopentyloxy. The more preferred R groups are those wherein the 4-position R group is methoxy, —O—$CF_3$, —O—$CHF_2$, or —O—$CH_2CHF_2$, and the 3-position R group is cyclopropylmethoxy or cyclopentyloxy.

In Formula (A) the most preferred $R_1$ groups are hydrogen, methyl or ethyl.

In Formula (B) the most preferred M groups are OH, tosyl and iodo.

The most preferred product of the process of this invention are those compounds which have a 3-cyclopentyloxy-4-methoxyphenyl substitution pattern.

Reaction Scheme I provides a diagrammatic overview of the intermediates and chemistries employed in this invention.

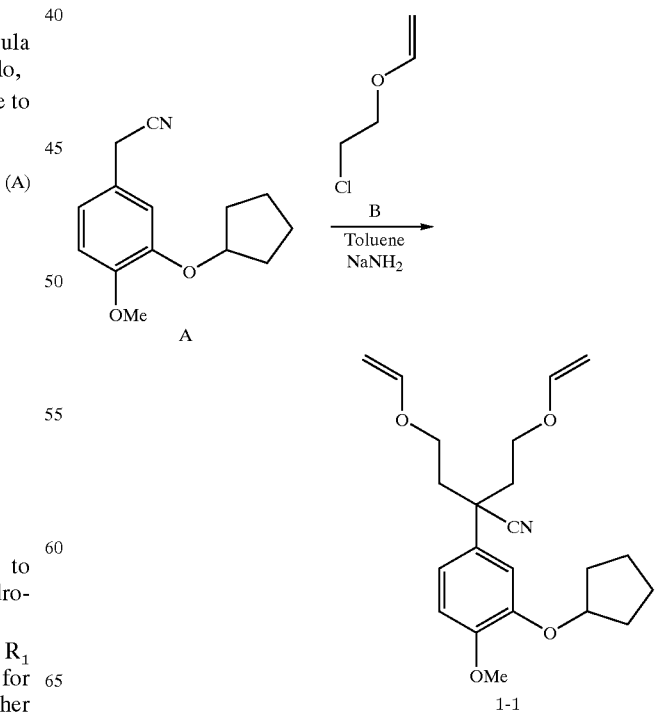

Scheme I 1-1

-continued
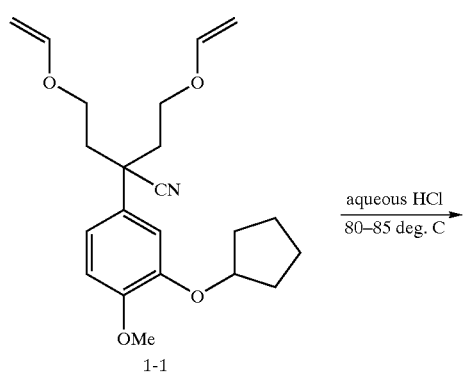
1-1
aqueous HCl
⎯⎯⎯⎯⎯⎯→
80–85 deg. C
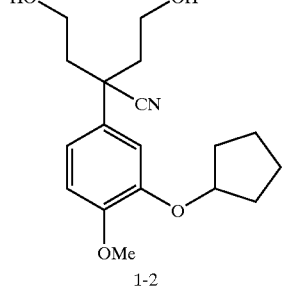
1-2
TsCl
⎯⎯⎯→
pyridine
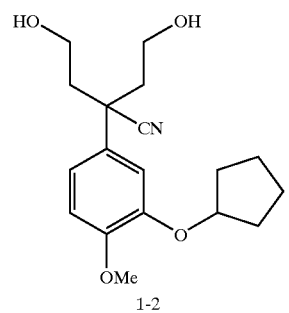
1-3
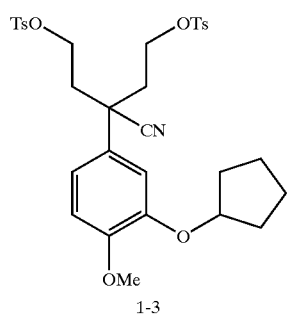
1-3
NaI
⎯⎯⎯→
acetone
-continued
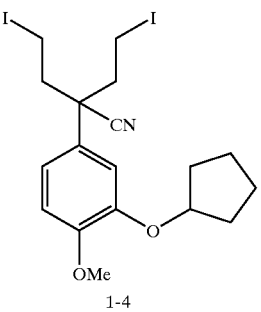
1-4
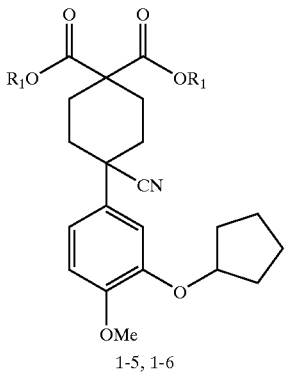
1-8 + C
$R_1O$—C(=O)—CH$_2$—C(=O)—$OR_1$
C
K$_2$CO$_3$
⎯⎯⎯→
DMF
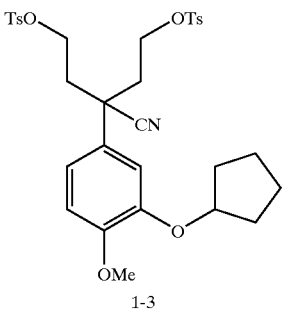
1-5, 1-6
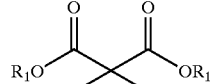
1-5, 1-6
LiCl
water
pyridine
⎯⎯⎯⎯→
DMSO
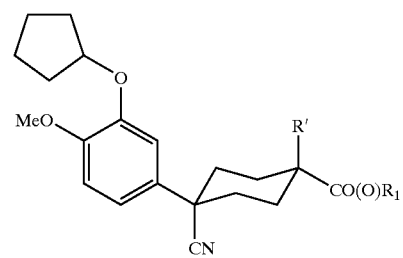

The starting material 3-cyclopentyloxy-4-methoxybenzeneacetonitrile is a known compound. See for example U.S. Pat. No. 5,449,686. The 2-chloroethylvinyl ether is commercially available (Aldrich). To effect the reaction, a strong base is charged to a reaction vessel containing a suitable non-polar solvent to which the vinyl ether is added. This mixture is heated to between about 30 to 70° C. and charged with the benzeneacetonitrile (A) pre-dissolved in the same solvent as the base and the vinyl ether. Toluene is a preferred solvent. A preferred base is sodium amide. The amount of base is equivalent, on a molar basis, to that of the vinyl ether. Both are used in about a three-fold excess relative to the substrate. After the benzeneacetonitrile has been charged to the reaction flask, the solution is further heated to around 80° C. more or less. Usually the reaction is complete in about 30 minutes to 2 hours. The product (1-1) is isolated using standard procedures.

The bis 2-hydroxyethyl compound (1-2) is prepared by treating the vinyl ether moiety prepared as per the preceding paragraph with a strong mineral acid in an aqueous solvent. For example water can be added to the 2-(ethenyloxy)ethyl compound (1-1), heating that combination to about 70–90° C. and then adding a molar excess of a mineral acid such as HCl or the like. A preferred set of conditions is one where the 2-(ethenyloxy)ethyl is treated with water and heated to about 80° C. more or less followed by the addition of a 50% molar excess of concentrated HCl. Under these conditions the reaction is complete in 5–20 minutes.

To obtain the halogenated compound 1-4, the diol is converted to a group which can be displaced by a halide ion. For example the diol can be converted to a tosylate, mesylate, or the like, by treating the diol with reagents and under conditions which form the tosylate, etc. By way of example the diol is dissolved in an organic solvent and treated with an excess of p-toluenesulfonyl chloride at room temperature for 3–7 hours. Preferably the reaction is run in pyridine with about a 2.5 molar excess of the p-toluenesulfonyl chloride.

This tosylate (or mesylate, triflate, etc) (1-3) is converted to the di-halo 1-4 by dissolving it in a polar aprotic solvent, and adding a weak base and a halide salt. This mixture is heated to reflux for a number of hours, for example overnight. A preferred solvent is acetone or dimethyl formamide. A preferred halide salt is sodium or lithium iodide though other sodium or potassium salts of fluorine, chlorine and bromine can be used as well. A 2 to 6-fold excess of the halide salt is preferred. Refluxing overnight usually effects completion of the reaction.

Forming the cyclohexane dicarboxylates or diacids 1-5 and 1-6 is effected by charging the di-halo compound (1-4) to a solution of a dialkyl malonate or malonic acid and a weak base in a dipolar aprotic solvent. This slurry is stirred for an extended period of time at an elevated temperature, for example overnight. More specifically sodium or potassium carbonate is combined with the likes of dimethyl malonate in a solvent such as dimethylformamide. Then the di-halo 1-4 is added and the resulting slurry is stirred overnight at about 75–95° C. or so. The malonate is added in about a 1:1 molar ratio to that of the di-halo compound.

The diester may be saponified to give the diacid, though this step is not illustrated in Scheme I. This is accomplished by treating the diester with an aqueous base in a water-miscible solvent. For example the diester is charged to a reaction vessel containing the likes of tetrahydrofuran to which is added water and an alkali hydroxide base such as lithium hydroxide. This solution is heated at reflux for a number of hours, for example overnight.

Decarboxylating the diester or diacid to get the mono-ester or mono-acid is accomplished by dissolving the diester in the likes of dimethylsulfoxide, adding about an equivalent of a base such as pyridine, about 3 equivalents of water and about 3 equivalents of a salt such as lithium chloride. This solution is stirred for several hours at 100 to 150° C. or thereabouts for 4–8 hours. Product is extracted from an acidified aqueous solution and further purified by conventional means. The product is a mixture of cis and trans isomers in about a 1:1 ratio. The cis form of the ester or acid can be enriched by dissolving a mixture of isomers in a lower alkanol and treating that solution with the alkali metal salt of the alkanol. A preferred alkanol is t-butanol and a preferred alkali metal salt is potassium t-butanol. The acid may be obtained by saponifying the ester using a base and then acidifying the resulting salt with using a mineral acid, for example.

The following examples are provided to illustrate the invention. These illustrative examples are not intended to limit the claimed invention in any fashion.

EXAMPLES

Example 1

Preparation of 3-(Cyclopentyloxy)-α,α-bis[2-(ethenyloxy)ethyl]-4-methoxybenzeneacetonitrile A 1 L flask was charged with 150 mL of toluene, sodium amide (16.5 g, 0.38 mole, 2.9 equivalents), and 2-chloroethyl vinyl ether (41.9 g, 0.39 mole, 3.0 equivalents). The suspension was heated to 50° C., then charged with a solution of 3-cyclopentyloxy-4-methoxybenzeneacetonitrile (30 g, 0.13 mole, 1.0 equivalents) in 150 mL of toluene. The reaction was then carefully heated to 80° C. The progress was followed by HPLC (acetonitrile/0.1 N aqueous ammonium acetate at 65/35, 15 cm Beckman ODS Ultrasphere, 2 mL/min, 215 nm UV). After 60 minutes, the solution was poured into 1 L of water and 300 mL of t-butyl methyl ether. The layers were separated, the organic layer washed with water, then brine. The solvent was removed under reduced pressure to give a brown oil (52.1 g). The captioned compound was isolated by column chromatography (230–400 mesh silica gel, 10/1 hexane/ethyl acetate).

Mass spectrometry gave m/z=372 (M+H$^+$)$^+$;

($^1$H NMR, 300 MHz, CDCl$_3$, δ ppm) δ 1.55–1.65 (m, 2H, ring CH$_2$), δ 1.70–2.00 (m, 6H, ring CH$_2$'s), δ 2.2–3.5 (m, 4 H,(CH$_2$)$_2$CCN), δ 3.50–3.85 (m, 4H, CH$_2$O), δ 3.85 (s, 3H, OCH$_3$), δ 3.95–4.10 (m, 4H, CH$_2$ alkene), δ 4.8 (m, 1H, ring CH), δ 6.30–6.40 (m, CH, alkene), δ 6.85–7.0 (m, 3H, aromatic).

Example 2

Preparation of 3-(Cyclopentyloxy)-α,α-bis(2-hydroxyethyl)-4-methoxybenzeneacetonitrile Purified 3-(cyclopentyloxy)-α,α-bis[2-(ethenyloxy)ethyl]-4-methoxybenzeneacetonitrile (5 g, 13.5 mmol) was treated with water (50 mL) and heated to 80° C. with rapid stirring. Concentrated hydrochloric acid (1.85 mL, 22.2 mmol) was added and stirring was continued for 10 minutes. The solution was poured into ice water (50 mL) and methylene chloride (50 mL). The layers were separated, and the aqueous layer was extracted once with methylene chloride.

The combined organic layers were washed with water, then brine, and concentrated to a light yellow oil in quantitative yield. Structure and purity were confirmed by $^1$H NMR.

($^1$H NMR, 300 MHz, CDCl$_3$, δ ppm) δ 1.55–1.70 (m, 2H, ring CH$_2$), δ 1.75–1.95 (m, 6H, ring CH$_2$'s), δ 2.10–2.40 (m, 4H, (CH$_2$)$_2$CCN), δ 3.55–3.85 (m, 4H, CH$_2$O), 3.88 (s, 3H, OMe), δ 4.8 (m, 1H, ring CH), δ 6.80–7.00 (m, 3H, aromatic).

Example 3

Preparation of 3-(Cyclopentyloxy)-4-methoxy-α,α-bis[2-[[(4-methylphenyl)sulfonyl]oxy]ethyl]benzeneacetonitrile A 250 mL flask was charged with 3-(cyclopentyloxy)-α,α-bis(2-hydroxyethyl)-4-methoxybenzeneacetonitrile (6.4 g, 20.1 mmol), pyridine (65 mL), and p-toluenesulfonyl chloride (9.56 g, 50.2 mmol). The solution warmed slightly (exothermic), then was stirred at room temperature for 5 hours. The reaction was deemed complete by HPLC (acetonitrile/0.1 N aqueous ammonium acetate at 65/35, 15 cm Beckman ODS Ultrasphere, 2 mL/min, 215 nm UV). The reaction was poured into 100 mL of 5% HCl and 50 mL of methylene chloride. The layers were separated, and the organic layer was washed with 5% HCl until neutral. The neutralized organic layer was then washed once with brine and concentrated. The captioned compound was isolated as a white solid by crystallization from ethanol and t-butyl methyl ether.

Mass spectrometry gave m/z=645 (M+NH$_4^+$)$^+$;

($^1$H NMR, 300 MHz, CDCl$_3$, δ ppm) δ 1.55–1.70 (m, 2H, ring CH$_2$), δ 1.72–2.0 (m, 6H, ring CH$_2$'s), δ 2.20–2.45 (m, 4H, (CH$_2$)$_2$CCN), 2.45 (s, 3H, ar-CH$_3$), 3.85 (s, 3H, OMe), δ 3.85–4.28 (m, 4H, CH$_2$O), δ 4.75 (m, 1H, ring CH), δ 6.75–7.75 (11H indicated, aromatic).

Example 4

Preparation of 3-(Cyclopentyloxy)-α,α-bis(2-iodoethyl)-4-methoxybenzeneacetonitrile A 250 mL flask was charged with 3-(cyclopentyloxy)-4-methoxy-α,α-bis[2-[[(4-methylphenyl)sulfonyl]oxy]ethyl]benzeneacetonitrile (5.0 g, 7.97 mmol), acetone (75 mL), and sodium bicarbonate (50 mg). This solution was stirred well while sodium iodide (5.98 g, 39.9 mmol) was added, then heated to reflux overnight. The reaction was poured into aqueous ammonium chloride and sodium bisulfite, then extracted with t-butyl methyl ether. The organic layer was dried over sodium sulfate, then concentrated to a clear colorless oil. The captioned compound was crystallized from t-butyl methyl ether and hexanes to give a white solid.

Mass spectrometry gave m/z=540 (M+H$^+$)$^+$;

CHN analysis calculated for C$_{18}$H$_{23}$NO$_2$I$_2$ (539.12): C 40.10, H 4.30, N 2.60; found: C 40.06, H 4.30, N, 2.45.

($^1$H NMR, 300 MHz, CDCl$_3$, δ ppm) δ 1.55–1.70 (m, 2H, ring CH$_2$), δ 1.75–2.05 (m, 6H, ring CH$_2$'s), δ 2.35–2.62 (m, 4H, (CH$_2$)$_2$CCN), δ 2.8 (m, 2H, CH$_2$I), δ 3.15 (m, 2H, CH$_2$I), 3.87 (s, 3H, OMe), δ 4.8 (m, 1 H, ring CH), δ 6.85 (s, 1H, aromatic), δ 7.18–7.30 (m, 2H, aromatic).

Example 5

Preparation of Dimethyl 4-cyano-4-[3-(cyclopentyloxy)-4-methoxyphenyl]-1,1-cyclohexanedicarboxylate and Diethyl 4-cyano-4-[3-(cyclopentyloxy)-4-methoxyphenyl]-1,1-cyclohexanedicarboxylate A 125 mL flask was charged with 60 mL of dimethylformamide, potassium carbonate (5.02 g, 36.4 mmol, 3.6 equivalents), dimethylmalonate (1.33 g, 10.1 mmol. 1.0 equivalents), and then 3-(cyclopentyloxy)-α,α-bis(2-iodoethyl)-4-methoxybenzeneacetonitrile (6.0 g, 11.1 mmol, 1.1 equivalents). The slurry was stirred at 80° C. overnight. The completed reaction was poured into 50 mL of water and 50 mL of t-butyl methyl ether. The organic layer was extracted three times with water, then once with brine. The product was isolated by column chromatography (Flash silica [230–400 mesh], 80/20 hexanes/ethyl acetate). Alternatively it was crystallized from hexanes/ethyl acetate (3/1) to give white crystals. The diethyl derivative was prepared using the same procedure.

Dimethyl Ester:

Mass spectrometry gave m/z=416 (M+H$^+$)$^+$;

CHN analysis calculated for C$_{23}$H$_{29}$NO$_6$ (539.12): C 66.49, H 7.04, N 3.37; found: C 66.24, H 6.94, N, 3.33.

($^1$H NMR, 300 MHz, CDCl$_3$, δ ppm) δ 1.55–1.67 (m, 2H, ring CH$_2$), δ 1.75–2.60 (m, 14H, ring CH$_2$'s), 3.75 (s, 3H, CO$_2$Me), 3.78 (s, 3H, CO$_2$Me), 3.82 (s, 3H, OMe), δ 4.8 (m, 1H, ring CH), δ 6.80–7.02 (m, 3H, aromatic).

Diethyl Ester

Mass spectrometry gave m/z=444 (M+H$^+$)$^+$;

mp. 74.0–74.5;

($^1$H NMR, 300 MHz, CDCl$_3$, δ ppm) δ 1.20–1.38 (m, 6H, ethyl CH$_3$), δ 1.50–2.60 (m, 16H, ring CH$_2$'s), 3.85 (s, 3H, OMe), δ 4.65–4.85 (m, 4H, ethyl CH$_2$), δ 4.8 (m, 1H, ring CH), δ 6.80–7.05 (m, 3H, aromatic).

Example 6

Hydrolysis of the Diethyl Ester to the Diacid

A 25 mL flask was charged with tetrahydrofuran (5 mL), the diethyl ester (SB 220523, 0.5 g, 1.13 mmol, 1.0 equivalent), water (5 mL), and lithium hydroxide monohydrate (0.95 g, 22.6 mmol, 20 equivalents). The solution was stirred at reflux for 18 hours. The reaction was deemed complete by HPLC (15 cm Supelcocil LC-ABZ, 40/60/0.1 [acetonitrile/water/TFA], 1.5 mL/min., 215 nm UV). The reaction solution was then cooled and diluted with 10% HCl and t-butyl methyl ether. The layers were separated and the aqueous layer was washed once with t-butyl methyl ether. The organic layers were combined and washed with water and then brine. The solution was then concentrated to a tan solid. Water was removed by reconcentrating once with acetonitrile. The crude product was obtained in about 90% yield. The crude product showed residual ethyl ester (<5%) by HPLC and $^1$H NMR.

($^1$H NMR, 300 MHz, CDCl$_3$, δ ppm) δ 1.55–1.70 (m, 2H, ring CH$_2$), δ 1.75–2.35 (m, 12H, ring CH$_2$'s), δ 2.52–2.63 (m, 2H, ring CH$_2$), 3.85 (s, 3H, OMe), δ 4.8 (m, 1H, ring CH), δ 6.8–7.0 (m, 3H, aromatic).

Example 7

Decarboxylation of the Diester: Ethyl 4-cyano(3-cyclopentyloxy-4-methoxyphenyl)-cyclohexanecarboxylate A 100 mL flask was charged with dimethylsulfoxide (35 mL), dimethyl 4-cyano-4-[3-(cyclopentyloxy)-4-methoxyphenyl]-1,1-cyclohexanedicarboxylate (3.5 g, 8.43 mmol, 1.0 equivalent), water (0.455 g, 25,3 mmol, 3.0 equivalents), pyridine (0.66 g, 8.43 mmol, 1.0 equivalent), and lithium chloride (1.07 g, 25.3 mmol, 3.0 equivalents). The solution was stirred at 130° C. for 6.5 hours. The reaction solution was then cooled and diluted with 1% HCl and t-butyl methyl ether. The layers were separated and the organic layer was washed with water twice and with brine once. The solution was concentrated to a clear oil. Water was removed by reconcentrating once with methanol. The product was obtained in quantitative yield as a clear oil and as a mixture of cis and trans isomers in about a 1:1 ratio.

Mass spectrometry gave n/z=372 (M+H$^+$)$^+$;

($^1$H NMR, 300 MHz, CDCl$_3$, δ ppm) δ 1.29 (t, 3H, ethyl CH$_3$), δ 1.55–1.70 (m, 2H, ring CH$_2$), δ 1.75–2.30 (m, 14H, ring CH$_2$'s), δ 2.75–2.80 (m, 1H, CHCO$_2$Et), 3.85 (s, 3H, OMe), δ 4.13–4.22 (q, 2H, ethyl CH$_2$), δ 4.8 (m, 1 H, ring CH), δ 6.8–7.0 (m, 3H, aromatic).

Example 8

Preparation of 4-cyano-4-(3-cyclopentyloxy-4-methoxyphenyl)-cyclohexanecarboxylic Acid The isomeric mixture (approximately 1 to 1 ratio) of the methyl esters prepared in Example 5 (2.94 g, 8.2 mmol, 1.0 equivalent) was dissolved in t-butanol (30 mL) under a nitrogen atmosphere. Potassium t-butoxide (1.8 g, 16.5 mmol, 2.0 equivalent) was added and the mixture was stirred 618 hours to give a ratio of cis to trans isomers of 14 to 1. The same procedure was used to treat the ethyl esters and gave a ratio of 8 to 1. The ratios were monitored using HPLC (15 cm Supelcocil LC-ABZ, 40/60/0.1 [acetonitrile/water/TFA], 1.5 mL/min., 215 nm UV).

To hydrolyze the equilibrated ester product, two drops of water were added to the reaction solution and the solution was stirred until no ester could be detected. The reaction was then diluted with t-butyl methyl ether and 5% HCl (the pH of the aqueous layer was between 1–2). The layers were separated and the organic layer was washed with brine. The ratio of cis to trans acid was improved even further (to 121 to 1) by crystallizing the cis/trans misture from 20 ml of hexanes/ethyl acetate (3/1).

What is claimed is:

1. A process for preparing a compound of formula (I)

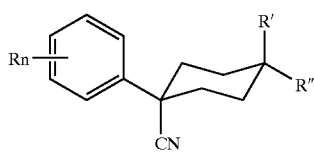

(I)

where

R is halo, C$_{1-6}$alkyl, C$_{1-6}$alkyl substituted with 1 to 4 halogens, C$_{1-6}$ alkoxy, C$_{1-6}$alkenyl,
—O—(CH$_2$)$_m$cycloalkyl of 3–6 carbons;
n is 1–5;
m is 0–6; and
one of R' or R" is hydrogen and the other is CO(O)X where X is hydrogen or C$_{1-6}$alkyl

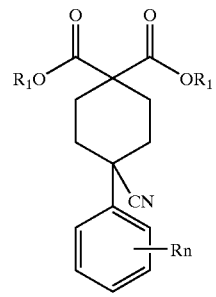

(A)

which process comprises decarboxylating the diacid or diester of Formula (A) where each R$_1$ is hydrogen or C$_{1-6}$alkyl-ester forming group of 1–6 carbon atoms and R and n are the same as for Formula (I) by treating the diacid or diester with about 1 equivalent of a base, about 3 equivalents of water and about 3 equivalents of an alkali salt in a suitable solvent and heated to between about 100 to 150° C. for about 4–8 hours.

2. The process of claim 1 wherein R$_1$ is hydrogen, methyl or ethyl and the base is pyridine and the salt is lithium chloride.

3. The process of claim 1 wherein n in R$_n$ is 2 and one group is substituted at the 3 position and the other group is substituted at the 4 position of the benzene ring of formula (I).

4. The process of claim 1 wherein R$_1$ is methyl, one of R$_n$ is methoxy, —O—CF$_3$, —O—CHF$_2$, or —O—CH$_2$CHF$_2$ and the other is C$_{4-6}$cycloalkyloxy.

5. The process of claim 1 wherein n in R$_u$ is 2 and one is 3-cylopentyloxy and a second Rn group is 4-methoxy.

6. A compound of formula (A)

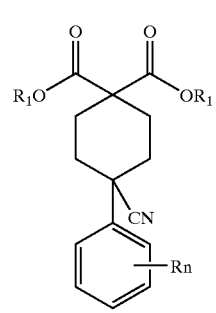

(A)

wherein

R is halo, C$_{1-6}$alkyl, C$_{1-6}$alkyl substituted with 1 to 4 halogens, C$_{1-6}$alkoxy, C$_{1-6}$alkenyl,
—O—(CH$_2$)$_m$cycloalkyl of 3–6 carbons;
n is 1–5;
m is 0–6;
R1 is hydrogen or a C$_{1-6}$alkyl-ester forming group of 1–6 carbon atoms.

7. A compound according to claim 6 wherein n in R$_u$ is 2 and R$_n$ is methoxy, —O—CF$_3$, —O—CHF$_2$, or —O—CH$_2$CHF$_2$ and the other is C$_{4-6}$cycloalkyloxy.

8. A compound according to claim 6 wherein n in Rn is 2 and one is 3-cyclopentyloxy and a second Rn group is 4-methoxy.

9. A compound of formula (B)

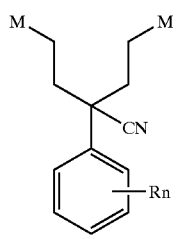

wherein n in $R_n$ is 2 and one $R_n$ group is 3-cyclopentyloxy and the second $R_n$ group is 4-methoxy and M is OH, an activated hydroxyl group, or halo.

10. A compound of formula C

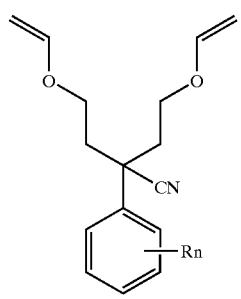

wherein n in $R_n$ is 2 and one is 3-cyclopentyloxy and a second Rn group is 4-methoxy.

11. A process for preparing a compound of Formula (I) according to claim 1, which process comprises

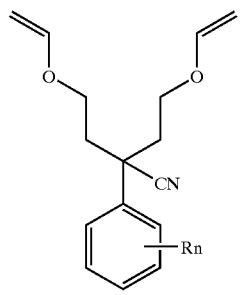

a. converting the vinylethyl ether of Formula (C)

R is halo, $C_{1-6}$alkyl, $C_{1-6}$alkyl substituted with 1 to 4 halogens, $C_{1-6}$alkoxy, $C_{1-6}$alkenyl, —O—$(CH_2)_m$cycloalkyl of 3–6 carbons;

n is 1–5;

m is 0–6;

to a compound of Formula (B)

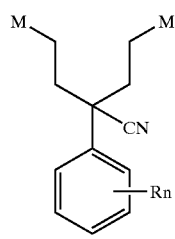

where M is OH, b. converting the hydroxyl group of Formula (B) to a compound of Formula (B) where M is a tosylate, mesylate or a triflate, c. converting the tosylate, mesylate or tiflate in Formula (B) to a compound of Formula (B) where M is halo, d. treating the di-halo compound with dialkyl malonate to obtain a compound of Formula (A)

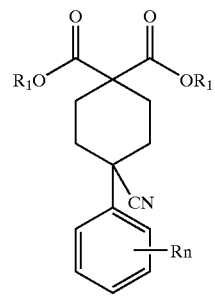

where $R_1$ is lower alkyl, e. optionally saponfying the diseater of Formula (A) to obtain a compound of Formula (A) where $R_1$ is hydrogen, and f. decarboxylating a compound of Formula (A) where $R_1$ is hydrogen or $C_{1-6}$alkyl to obtain a compound for Formula (I) where one of R' is hydrogen and the other is CO(O)X where X is $C_{1-6}$alkyl or hydrogen.

12. The process of claim 11 wherein n is $R_n$ is 2 and $R_n$ is methoxy, —O—$CF_3$, —O—$CHF_2$, or —O—$CH_2CHF_2$ and the other is $C_{4-6}$cycloalkyloxy, M is tosylate and thereafter iodo, and R1 is methyl or ethyl.

13. The process of claim 11 wherein n is $R_n$ is 2 and one is 3-cyclopentyloxy and the second is 4-methoxy.

* * * * *